United States Patent [19]
Walter

[11] 4,152,522
[45] May 1, 1979

[54] PROCESS FOR THE PREPARATION OF 2-BENZIMIDAZOLE CARBAMATES

[75] Inventor: Thomas J. Walter, Baton Rouge, La.

[73] Assignee: Ethyl Corporation, Richmond, Va.

[21] Appl. No.: 866,618

[22] Filed: Jan. 3, 1978

[51] Int. Cl.² ........................................... C07D 235/32
[52] U.S. Cl. .................................... 548/306; 260/454; 260/578; 560/159
[58] Field of Search ......................................... 548/306

[56] References Cited

U.S. PATENT DOCUMENTS

| | | | |
|---|---|---|---|
| 3,929,823 | 12/1975 | Beard et al. | 548/306 |
| 3,935,209 | 1/1976 | Beard et al. | 548/306 X |
| 3,997,553 | 12/1976 | Schlatter et al. | 548/306 |
| 4,010,272 | 3/1977 | Loewe et al. | 548/306 X |
| 4,093,732 | 6/1978 | Haugwitz | 548/306 X |

OTHER PUBLICATIONS

Challenger et al., J. Chem. Soc., 1928, pp. 1364, 1365 and 1368.

*Primary Examiner*—Richard Raymond
*Attorney, Agent, or Firm*—Donald L. Johnson; John F. Sieberth; James M. Pelton

[57] ABSTRACT

A process for preparing 2-benzimidazole carbamate compounds by condensing an alkyl cyano carbamate with an o-phenylenediamine produced by reacting an ortho-nitro-aniline with thiocyanogen followed by replacement of the cyanide with an alkyl group and then converting the nitro group to the amine.

11 Claims, No Drawings

PROCESS FOR THE PREPARATION OF 2-BENZIMIDAZOLE CARBAMATES

BACKGROUND OF THE INVENTION

This invention relates to a process for preparing 2-benzimidazole carbamate compounds. More particularly, this application describes a method for preparing alkyl 5alkylthio-2-benzimidazole carbamate compounds, also referred to as 5(6)-alkylthio-2-benzimidazole carbamate compounds. Such compounds are useful as the active ingredients to combat infections of certain parasites in animals. The process of this invention produces compounds which demonstrate excellent activity against gastro-intestinal parasites such as mouse pinworm and sheep nematodes, and against migratory states of *Ascaris suum* in mice. In particular, the compounds produced by the process of this invention have been found to posses useful anthelmintic properties, that is, broad spectrum activity against parasites of warm blooded animals, including both mature and immature parasitic forms. In particular, these compounds have been found to exhibit high activity against various helmintic infections of the intestinal tract of economically important animals, coupled with low systemic toxicity to the host animals.

For example, compounds produced by the process disclosed are generally effective in clearing mice of worm infections for laboratory purposes, among others: *Syphacia obvelata* and Appliculuris tetraptera (mouse pinworm), *Nematospiroides dubius* (mouse hookworm), and the migratory stages of *Ascaris suum*.

Other susceptible helminths include *Toxocara canis*, found in naturally infested dogs. Also, parasitic to this host are *Ancylostoma canium*, *Trichuris vulpis* (whipworm), and *Physalaptera spp.*

Compounds of this invention have been demonstrated as efficacious against parasites of pigs, such as the migratory stages of *Ascaris suum*, thus preventing the development of verminous pneumonia.

Compounds of this invention have also been demonstrated as efficacious against parasitic gastroenteritis in sheep, such as *Haemonchus contortus*, Ostertagia spp., Trichostrongylus spp., Nematodirus spp., *Trichuris ovis*, Cooperia spp., and *Strongyloides papillosus. Bunostomum trigonocephalum* and Oesophagostomum spp., are other important parasites of sheep.

In addition, compounds of this invention have also been found to have anthelmintic activity against parasites causing lungworm infections of animals. These parasites are of the Dictyocaulidae, Metastrongylidae, Protostrongylidae, and Filaroididae families, especially the genus Dictyocaulus which are prevalent in sheep, cattle and horses. They are particularly resistant to standard anthelmintic agents. Metastrongylus is important in pigs, Protostrongylus in sheep and goats, and Filaroides in cats and dogs. Certain lung-worms have been reported to be vectors for the influenza virus in swine.

Compounds of this type have been found to be especially useful and data supporting this use can be found in U.S. Pat. Nos. 3,915,986, 3,905,991, 3,574,845, 3,984,561, 3,997,553, 4,005,202, 4,010,272, 4,002,640, and 3,993,769, all of which are incorporated herein by reference as if fully set forth. Accordingly, the use, dosages and various formulations for compounds in accord with invention are fully disclosed in the prior art.

DISCLOSURE OF THE INVENTION

The process of the present invention provides an advantageous process for producing compounds known in the prior art. In one aspect of the present invention, there is provided a process for the preparation of a 2-benzimidazole carbamate compound having the general formula

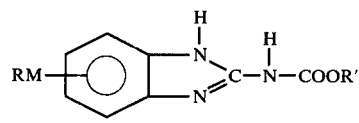

in which R and R' are independently selected from groups having 1 to about 4 carbon atoms and M is oxygen or sulphur, said process comprising the steps of (a) thiocyanating ortho-nitro-aniline with an inorganic thiocyanate, such as ammonium or alkali metal thiocyanate, in the presence of an oxidation agent, such as a halogen selected from chlorine and bromine, to form a solid thiocyano-2-nitroaniline product which is filtered from the reaction mixture;

(b) alkylating the thiocyanate prepared in step (a) with an alkyl halide and an alkyl alcohol in which both of said alkyl groups are the same and are selected from those having 1 to about 4 carbon atoms, said alkylation being conducted in the presence of at least 1 equivalent of alkali metal cyanide or alkaline earth metal cyanide and a phase transfer catalyst so that an alkylthio-2-nitroaniline is formed;

(c) reducing the nitro group in said thioalkyl-2-nitroaniline prepared in said step (b) by reacting with an aqueous alkali metal sulfide selected from sodium sulfide and sodium disulfide at elevated temperatures and in an inert atmosphere until an alkylthio-o-phenylenediamine is formed; and (d) condensing said alkylthio-o-phenylenediamine with an alkyl cyano carbamate or an alkali or alkaline earth metal salt thereof, in which the alkyl group has from 1 to about 4 carbon atoms, in the presence of a sufficient amount of acid to maintain the pH of the reaction mixture at about 4 whereby said benzimidazole-2-carbamate compound is formed.

The overall process of the present invention can be summarized by the following schematic chemical transformations:

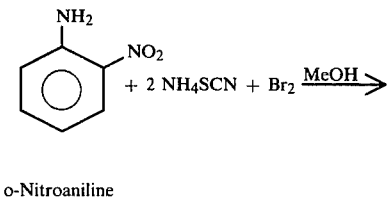

o-Nitroaniline

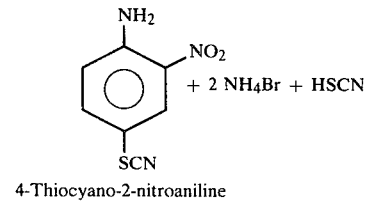

4-Thiocyano-2-nitroaniline

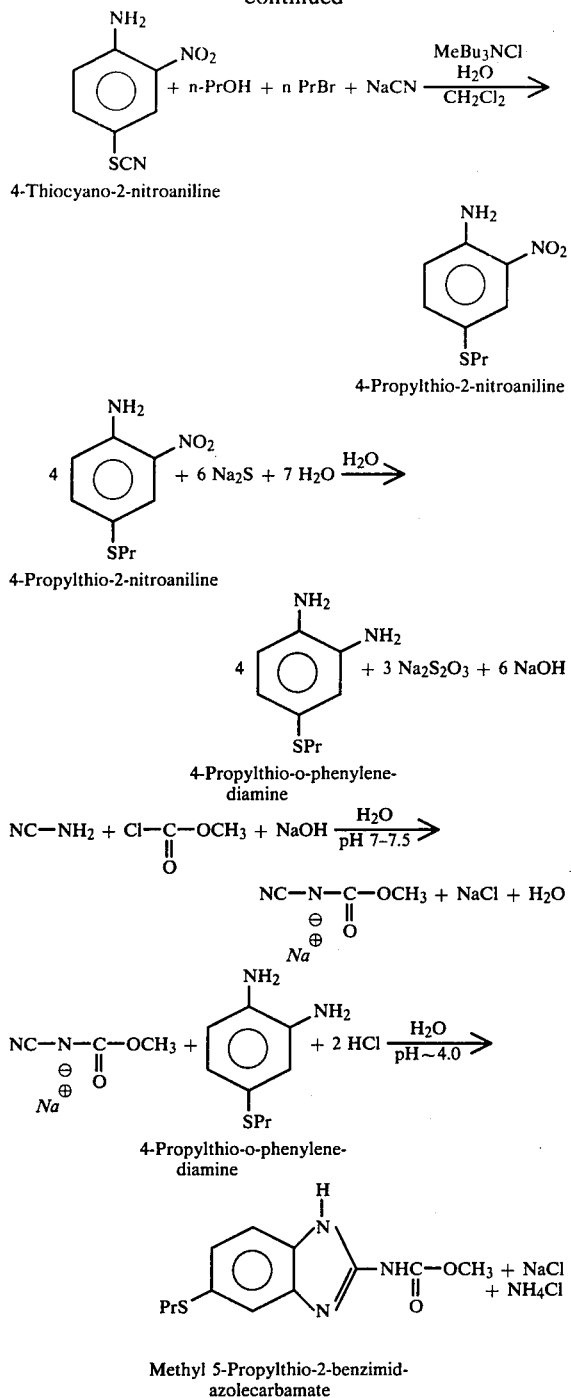

The four reactions are characterized by excellent yields, relatively mild reaction conditions, and exceptionally low byproduct formation. The following examples illustrate the process for the present invention.

EXAMPLE I

Preparation of 4-thiocyano-2-nitroaniline—A 13.8 g portion of o-nitroaniline and 18.3 g of ammonium thiocyanate were dissolved in 110 ml of methanol. The reaction mixture was cooled to 3°–5° C. A solution of 17.6 g of bromine in 20 ml of methanol that had been saturated with sodium bromide was added to the reaction mixture over a 45 minute period while maintaining the temperature of the reaction mixture at 3°–5° C. The reaction slurry was stirred for one hour at 0–5° C. after the addition was complete. The ice bath was removed and the reaction slurry was allowed to warm to room temperature. The slurry was poured over 500 ml of an ice-water mixture and stirred until all the ice melted. The solids were filtered, washed three times with cold water, and allowed to air dry. The weight of crude product was 18.38 g. This product contained 94.7% 4-thiocyano-2-nitroaniline as determined by HPLC analysis, 89% yield from o-nitroaniline. Pure 4-thiocyano-2-nitroaniline can be prepared by recrystallization from toluene, mp. 116.5°–117° C., IR and NMR consistent.

EXAMPLE II

Preparation of 4-thiocyano-2-nitroaniline—The experiment was conducted as in Example I except that 7.8 g of chlorine gas was bubbled into the chilled reaction mixture over a 35 minute period. After the same workup as in Example I, 16.75 g of crude dry product was obtained. This product assayed 90% giving 77% yield of 4-thiocyano-2-nitroaniline from o-nitroaniline.

EXAMPLE III

Preparation of 4-propylthio-2-nitroaniline—To 20 ml of methylene chloride was added 2.0 g of 4-thiocyano-2-nitroaniline, 3.72 g of n-propanol, 7.58 g of n-propyl bromide, and 0.16 g of an aqueous solution of 75% methyl tributylammonium chloride. The reaction mixture was heated to reflux in a 45° bath and 12 g of an aqueous solution of 25% sodium cyanide was added. The reaction mixture was refluxed for 4 hours with moderate agitation and then cooled. The phases were separated. The organic phase was found to contain 21.1 g (97% yield) of 4-propylthio-2-nitroaniline by HPLC assay. Pure 4-propylthio-2-nitroaniline can be prepared by evaporating the methylene chloride and crystallizing from chloroform-hexane at $-50°$ to $-70°$ C. Pure 4-propylthio-2-nitroaniline is an orange crystalline solid, m.p. 36.5°–38° C., IR and NMR consistent.

EXAMPLE IV

Preparation of 4-propylthio-o-phenylenediamine—A mixture of 8.0 g of 4-propylthio-2-nitroaniline, 40.8 g of sodium sulfide nonahydrate and 100 ml of water was refluxed for 10.75 hours under nitrogen. The reaction mixture was cooled and 25 ml of methylene chloride was added. The layers were separated and the aqueous phase was washed with three 20 ml portions of methylene chloride. The methylene chloride from the combined undried organic fraction was evaporated. The residual solids were taken up in 25 ml of methanol and used in Example V. All operations in this Example IV were conducted under an inert atmosphere to prevent oxidation of the air-sensitive 4-propylthio-o-phenylenediamine. The methanol solution was analyzed by gas chromatography to contain 98.5% 4-propylthio-o-phenylenediamine and 0.8% 4-propylthio-2-nitroaniline. In similar experiments, absolute yields of 90–100% were determined by gas chromatography with the addition of biphenyl to the reaction mixture as an internal standard.

EXAMPLE V

Preparation of methyl 5-propylthio-2-benzimidazole carbamate—A 1.82 g portion of cyanamide was dissolved in 10 ml of water. Methyl chloroformate, 4.64 g, and 6.34 g of 50% aqueous sodium hydroxide in 6 ml of water were added simultaneously so as to maintain the pH at approximately 7 as determined by a pH meter. The reaction mixture was stirred at 50° C. for one hour. A portion of 7.4 g of concentrated hydrochloric acid in 7 ml of water was added until the pH was 4. The methanol solution of 4-propylthio-o-phenylenediamine from Example IV was added at once. More of the hydrochloric acid solution was added to adjust the pH to 4. The reaction mixture was heated to distill the methanol. As methanol was nearly removed more hydrochloric acid solution was added to keep the pH at 4. Water was added from time to time to keep the slurry from becoming too thick. The reaction slurry was heated at 100° C. for one hour after the methanol had been removed. The reaction slurry was cooled, filtered and washed liberally with water. The solids were air dried to produce 8.77 g of crude methyl 5-propylthio-2-benzimidazole carbamate. The crude solids were washed 3 times with cold acetone and dried to produce 7.52 g of product assaying 97% methyl-5-propylthio-2-benzimidazole carbamate by HPLC, 73% yield from the 4-propylthio-2-nitroaniline employed in Example IV.

EXAMPLE VI

Preparation of methyl 5-propylthio-2-benzimidazole carbamate—4-Thiocyano-2-nitroaniline was prepared as described in Example I using 13.8 g of o-nitroaniline and 18.3 g of ammonium thiocyanate dissolved in 80 ml of methanol and adding 17.6 g of bromine in 10 ml of methanol saturated with sodium bromide. After work up and filtering a wet cake of crude product weighing 44 g was obtained. This wet cake along with 32.5 g of n-propanol, 66.4 g of n-propyl bromide, 1.41 g of an aqueous solution of 75% methyl tributyl ammonium chloride, 104.6 g of an aqueous solution of 25% sodium cyanide and 175 ml of methylene chloride was refluxed with moderate agitation for 5 hours as described in Example III. The phases were separated, the volatile components were evaporated and the crude 4-propylthio-2-nitroaniline was added to a flask containing 88.2 g of sodium sulfide nonahydrate and 175 ml of water. The reaction mixture was refluxed for 13 hours as described in Example IV. After work up the methanol solution of crude 4-propylthio-o-phenylenediamine was added to the sodium salt of methyl cyanocarbamate which was prepared as in Example V from 4.35 g of cyanamide, 11.1 g of methyl chloroformate and 14.4 g of 50% aqueous sodium hydroxide. As in Example V, the methanol was removed, the pH was maintained at 4, the product was filtered and washed with water and acetone and allowed to air dry. The weight of crude dry product was 17.2 g which assayed 90% methyl 5-propylthio-2-benzimidazole carbamate, 58% yield from o-nitroaniline.

The above described process will, of course, be subject to variations in conditions and reactants which are well within the skill of the art. Processes for preparing many of the benzimidazole carbamates disclosed in the incorporated references will be clear to one skilled in the art after reading this disclosure. Therefore, it is desired to limit the invention only by the lawful scope of the following claims.

What is claimed is:

1. A process for the preparation of a 2-benzimidazole carbamate compound having the general formula

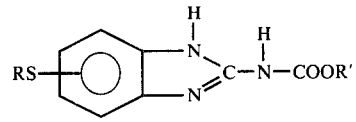

in which R and R' are independently selected from alkyl groups having 1 to about 4 carbon atoms, said process comprising the steps of
 (a) thiocyanating ortho-nitro-aniline with ammonium thiocyanate in the presence of a halogen selected from chlorine and bromine to form a solid thiocyano-2-nitroaniline product which is filtered from the reaction mixture;
 (b) alkylating the thiocyanate prepared in step (a) with an alkyl halide and an alkyl alcohol in which both of said alkyl groups are the same and are selected from those having 1 to about 4 carbon atoms, said alkylation being conducted in the presence of at least 1 equivalent of alkali metal cyanide or alkaline earth metal cyanide and a phase transfer catalyst so that a thioalkyl-2-nitroaniline is formed;
 (c) reducing the nitro group in said thioalkyl-2-nitroaniline prepared in said step (c) by reacting with an aqueous alkali metal sulfide selected from sodium sulfide and sodium disulfide at elevated temperatures an in an inert atmosphere until a thioalkyl-o-phenylenediamine is formed; and
 (d) condensing said thioakyl-o-phenylenediamine with an alkali or alkaline earth metal salt of alkyl cyano carbamate, in which the alkyl group has from 1 to about 4 carbon atoms at reflux in the presence of a sufficient amount of acid to maintain the pH of the reaction mixture at about 4 to form said benzimidazole-2-carbamate compound.

2. The process of claim 1 wherein said 2-benzimidazole carbamate compound is a 5-alkylthio-2-benzimidazole carbamate.

3. The process of claim 2 wherein said alkyl group is a lower alkyl group having from 1 to about 4 carbon atoms.

4. The process of claim 2 wherein said 2-benzimidazole carbamate is a lower alkyl 5-propylthio-2-benzimidazole carbamate.

5. The process of claim 1 wherein said 2-benzimidazole carbamate is methyl 5-propylthio-2-benzimidazole carbamate.

6. The process of claim 1 wherein said step (a) is conducted in the presence of bromine.

7. The process of claim 1 wherein said step (b) is conducted with a propyl halide and propyl alcohol.

8. The process of claim 1 wherein said step (b) is conducted in the presence of a sodium cyanide.

9. The process of claim 1 wherein said step (b) is carried out with a phase transfer catalyst selected from tetrabutyl ammonium chloride and methyl tributyl ammonium chloride.

10. The process of claim 1 wherein said step (c) is carried out with aqueous sodium sulfide.

11. The process of claim 1 wherein said step (d) is carried out with the sodium salt of methyl cyano carbamate.

* * * * *